(12) United States Patent
Erickson et al.

(10) Patent No.: US 11,627,876 B2
(45) Date of Patent: Apr. 18, 2023

(54) PRESSURE SENSING RETRACTOR FOR MEASURING ORBITAL COMPARTMENT PRESSURE OF AN EYE

(71) Applicant: The Board of Trustees of the Leland Stanford Junior University, Stanford, CA (US)

(72) Inventors: Benjamin Peter Erickson, Palo Alto, CA (US); Henry Bair, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 420 days.

(21) Appl. No.: 16/900,431

(22) Filed: Jun. 12, 2020

(65) Prior Publication Data

US 2020/0390332 A1 Dec. 17, 2020

Related U.S. Application Data

(60) Provisional application No. 62/860,955, filed on Jun. 13, 2019.

(51) Int. Cl.
*A61B 3/16* (2006.01)
*A61B 17/02* (2006.01)

(52) U.S. Cl.
CPC ............ *A61B 3/16* (2013.01); *A61B 17/0231* (2013.01); *A61B 2562/0247* (2013.01)

(58) Field of Classification Search
CPC ....... A61B 3/16; A61B 17/02; A61B 17/0206; A61B 17/0218; A61B 17/0231; A61B 2562/0247; A61F 9/007
See application file for complete search history.

(56) References Cited

U.S. PATENT DOCUMENTS

| | | | | |
|---|---|---|---|---|
| 4,972,825 | A * | 11/1990 | Vescovo, Jr. | ...... A61B 1/00142 383/103 |
| 7,985,180 | B2 * | 7/2011 | Brown | ..................... A61B 1/32 600/235 |
| 2006/0135864 | A1 * | 6/2006 | Westerlund | .............. A61B 3/16 600/587 |
| 2013/0215383 | A1 | 8/2013 | Siminou | |

FOREIGN PATENT DOCUMENTS

DE 202004021679 9/2010

* cited by examiner

*Primary Examiner* — Tse W Chen
*Assistant Examiner* — Huong Q Nguyen
(74) *Attorney, Agent, or Firm* — Lumen Patent Firm

(57) ABSTRACT

A pressure sensing retractor device and method is provided for measuring orbital compartment pressure of an eye. The device uses nested claw-like retractors where the inner claw retractor is capable of pulling an eyelid of the eye of a patient, and the outer claw retractor is capable of sensing the orbital compartment pressure of the eye. The pressure sensing retractor outputs the force sensor signal as a continuous signal of the orbital compartment pressure of the eye. Embodiments of the invention can be applied towards analysis of orbital compartment syndrome, retrobulbar hemorrhage (RBH), and canthotomy/cantholysis. Unlike applanation tonometry, retractor placement with the retractor provided herein requires no specialized training. Ease of use can help facilitate appropriate clinical decision, especially in environments without immediate access to ophthalmic consultation.

12 Claims, 6 Drawing Sheets

PRESSURE SENSING RETRACTOR FOR MEASURING ORBITAL COMPARTMENT PRESSURE OF AN EYE

CROSS-REFERENCE TO RELATED APPLICATIONS

This application claims priority from U.S. Provisional Patent Application 62/860,955 filed Jun. 13, 2019, which is incorporated herein by reference.

FIELD OF THE INVENTION

This invention relates to methods and devices for orbital pressure sensing of the eye.

BACKGROUND OF THE INVENTION

Clinically significant retrobulbar hemorrhage (RBH) is a potentially blinding consequence of craniofacial trauma, endoscopic sinus surgery, and periocular surgery such as blepharoplasty, or may rarely occur spontaneously in the setting of chronic anticoagulation or clotting disorders, such as hemophilia or Von Willebrand disease.

The anterior confine of the bony orbit is a minimally distensible sling formed by the orbital septum, tarsal plates, and canthal tendons. Any significant increase in retrobulbar volume, such as from hematoma formation, therefore results in orbital compartment syndrome (OCS). When intra-orbital pressure exceeds arterial perfusion pressure, the retina and optic nerve become ischemic. Irreversible visual loss results if this unfavorable gradient is not rapidly reversed. Observational studies and animal models suggest that permanent ischemic changes begin within 60 minutes, while significant central acuity loss can occur within 1.5 to 2 hours. Given that most ophthalmic and craniofacial injuries are not fully evaluated until the secondary trauma survey, much of this time has likely elapsed before OCS is first identified, placing a high premium on rapid clinical decision making.

Lateral canthotomy and inferior cantholysis, when properly performed, reliably lowers orbital compartment pressures to a safe level in many patients, and is the gold standard first line intervention for clinically significant OCS. The technique has been described in the trauma literature, but guidelines for performance remain vague and many practice settings—even those to which ocular and craniofacial trauma cases are likely to present lack access to ophthalmic specialty support within the optimal timeframe for intervention. This procedure is therefore often performed by non-ophthalmic providers.

Intraocular pressure (TOP) is typically used as a proxy for orbital compartment pressure in emergency settings to determine which patients require intervention. Many providers, however, are not trained to assess this accurately, even assuming that the appropriate equipment is available to perform applanation tonometry. Devices designed for use in standard office settings with well patients, may not perform optimally in a trauma setting.

A portable digital applanation tonometer (Tono-pen) requires that the examiner lightly tap the tip of the device against the patient's anesthetized central corneal several times to obtain an average intraocular pressure value. Reliably performing these maneuvers in the context of trauma, particularly in the setting of eyelid edema/hematoma, poor patient cooperation, or the Bell's supraduction reflex, is challenging, especially for those not using this device on a daily basis. Any effort to manually open the patient's eyelids for tonometry may artifactually increase TOP readings and produce misleading conclusions.

When canthotomy/cantholysis is performed by an inexperienced provider, it also may be difficult to determine whether TOP measurements remain high because of the severity of the retrobulbar hemorrhage and need for more aggressive interventions, or because of inadequate release of the tarsoligamentous sling in the first place. Staged superior cantholysis and other additional measures are required in some patients to relieve the compartment syndrome adequately.

The present invention advances the art by addressing the current shortcomings to reliable measure orbital compartment pressure of the eye.

SUMMARY OF THE INVENTION

A pressure sensing retractor device and method is provided for measuring orbital compartment pressure of an eye. The device has an inner retractor blade with an inner retractor blade an inner claw-like curved retractor, and an outer retractor blade with an outer claw-like curved retractor where the claws are nested with each other and distanced from each at a separation distance. The pressure sensing retractor has a force sensor which is situated such to sense that when the inner claw-like curved retractor is pulling an eyelid of the eye of a patient, the outer claw-like curved retractor is sensing the orbital compartment pressure of the eye. The pressure sensing retractor outputs the force sensor signal as a continuous signal of the orbital compartment pressure of the eye. Embodiments of the invention can be applied towards analysis of orbital compartment syndrome, retrobulbar hemorrhage (RBH), and canthotomy/cantholysis.

Advantages of embodiments of this invention are, for example and first, portable digital applanation tonometry is currently used as a proxy measure for orbital compartment pressure, but it remains challenging for inexperienced users to obtain reliable and actionable data with this measurement modality. Second, radiographic assessment of RBH cannot determine clinical significance under most circumstances, and proxy measures of compartment syndrome—such as globe tenting—are only seen in a limited percentage of advanced cases. Third, other measures for assessing orbital compartment pressure, such as evaluation of retinal perfusion on funduscopic examination, require ophthalmic expertise unobtainable without specialty consultation.

Unlike applanation tonometry, retractor placement with the retractor provided herein requires no specialized training. Rather than obtaining pressure values over random millisecond intervals, which is highly vulnerable to sampling bias, the lowest measurement obtained with the retractor of this invention can be taken as an accurate reflection of OCP, providing reliable and actionable information to guide emergent canthotomy/cantholysis and other indicated procedures. Ease of use can help facilitate appropriate clinical decision, especially in environments without immediate access to ophthalmic consultation.

DETAILED DESCRIPTION

The present invention provides a pressure sensing retractor that can be inserted between a patient's upper or lower eyelid and globe of the eye to directly measure orbital compartment pressure without having to be precisely oriented with respect to the central cornea. In fact, the pressure sensing retractor may be placed laterally, reducing the risk of inadvertent corneal abrasion. Unlike tonometry, measurements with the pressure sensing retractor are continuous for as long as the retractor tip remains in place. This is in contrast to applanation tonometry, which is recorded over random millisecond intervals, and therefore highly vulnerable to sampling bias. The lowest pressure measurement obtained by the pressure sensing retractor, with the patient not squeezing, can be taken as the most accurate measure of compartment pressure. This provides reliable and actionable information to guide canthotomy/cantholysis and other indicated procedures. Unlike using a digital applanation tonometer properly, placing the blades of the retractor behind an eyelid requires little specialized training.

Figure 1:
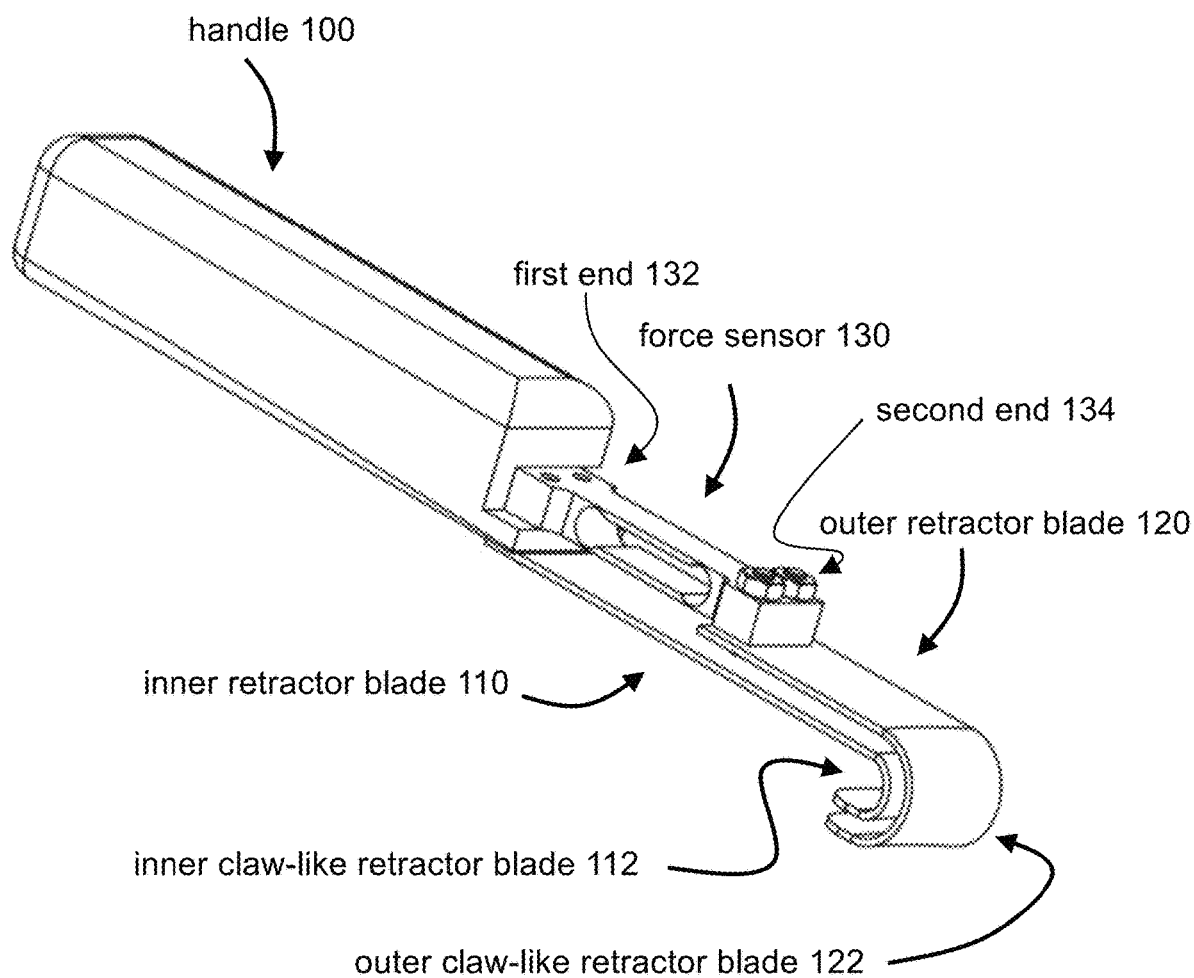
FIG. 1 shows a pressure sensing retractor according to an exemplary embodiment of the invention. Handle=100, Inner retractor blade=110, Inner claw-like curved retractor (aka Inner curved retractor blade)=112, Outer retractor blade=120, Outer claw-like curved retractor blade (aka Outer curved retractor blade)=122, Force sensor=130, First End=132, Second End=134.
Figure 2:
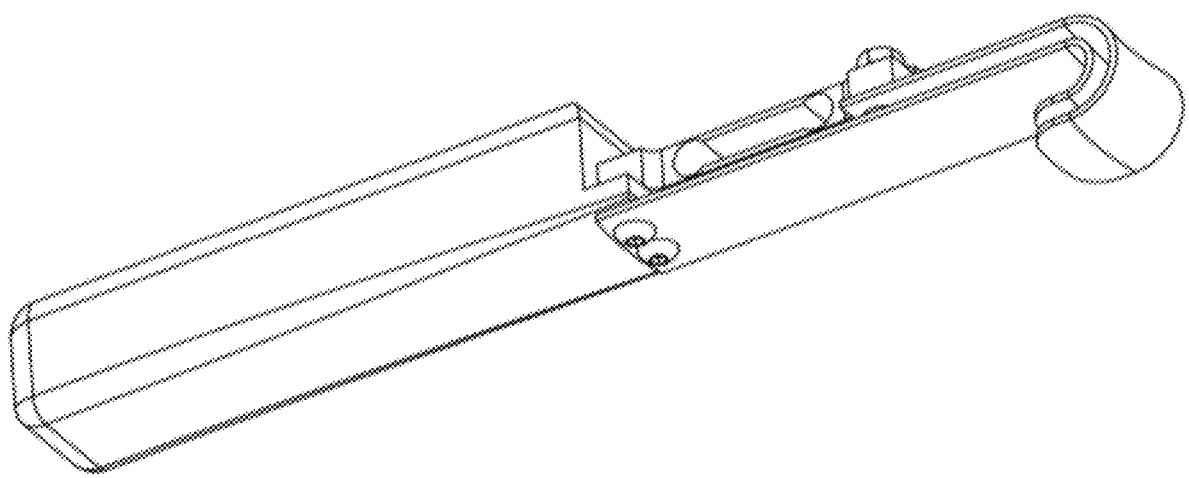
FIG. 2 shows the same a pressure sensing retractor as in FIG. 1 in a different view and according to an exemplary embodiment of the invention.
Figure 3:
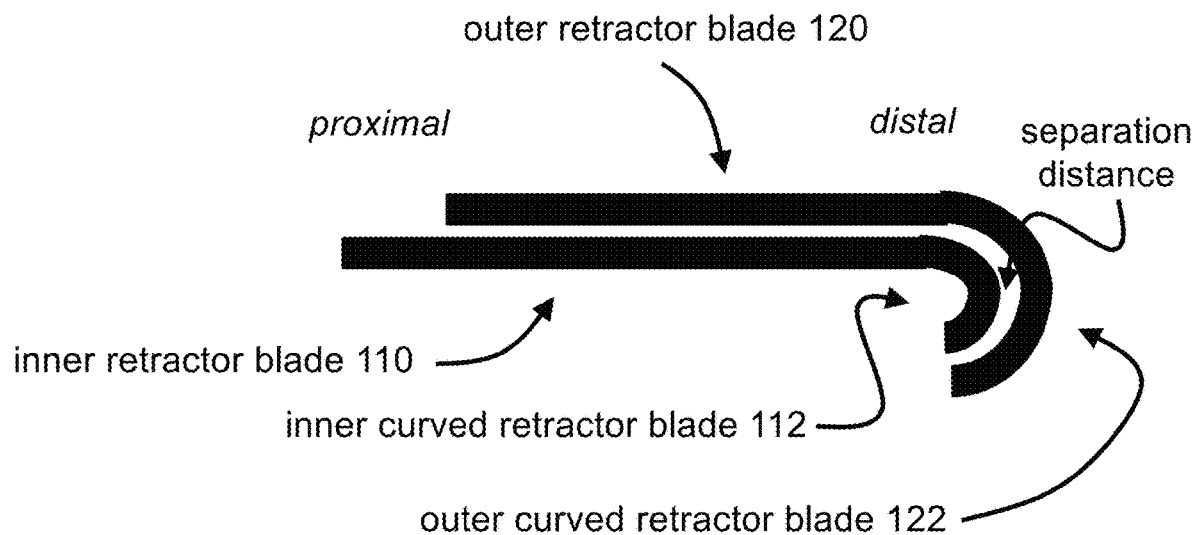
FIG. 3 shows the inner and outer blade of the pressure sensing retractor according to an exemplary embodiment of the invention.
Figure 4:
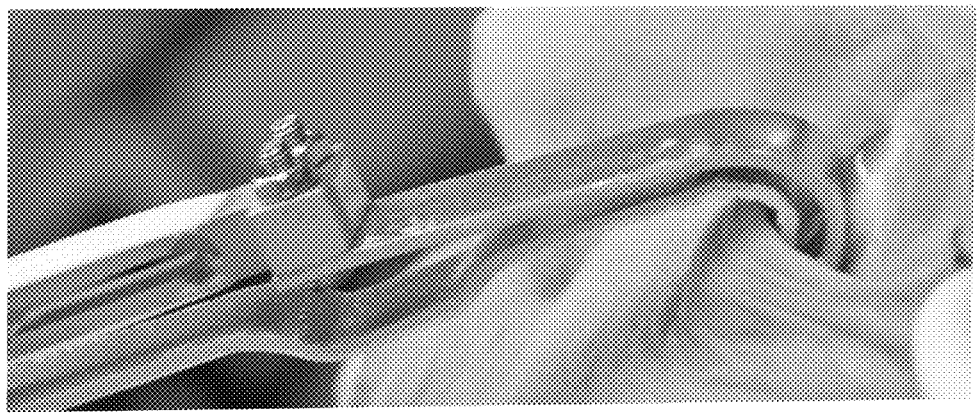
FIG. 4 shows the pressure sensing retractor in use and positioned between the lower eyelid and the sclera according to an exemplary embodiment of the invention.
Figure 5:
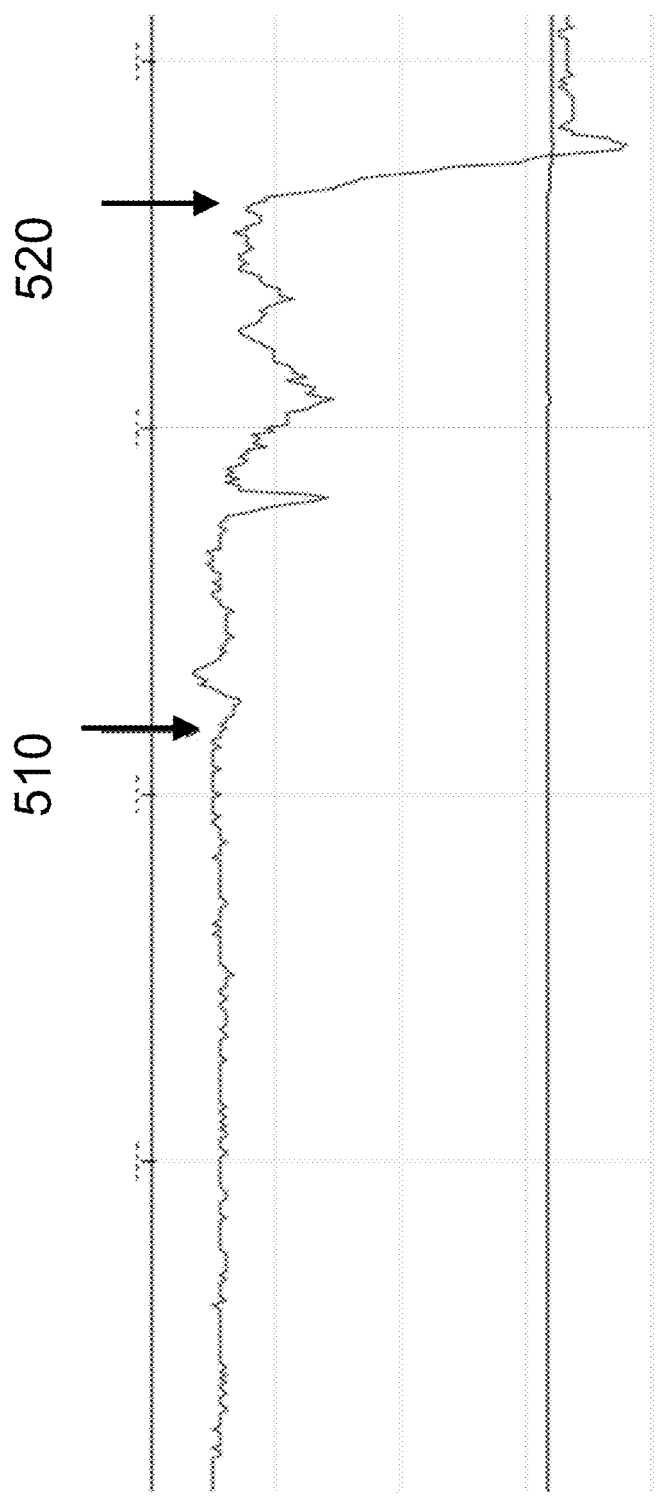
FIG. 5 shows according to an exemplary embodiment of the invention continuous pressure monitoring by the pressure sensing retractor demonstrated rapid dissipation of pressure following successful release of the tarsoligamentous sling. Arrow 510 indicates the initiation of canthotomy and arrow 520 indicates its completion.
Figure 6:
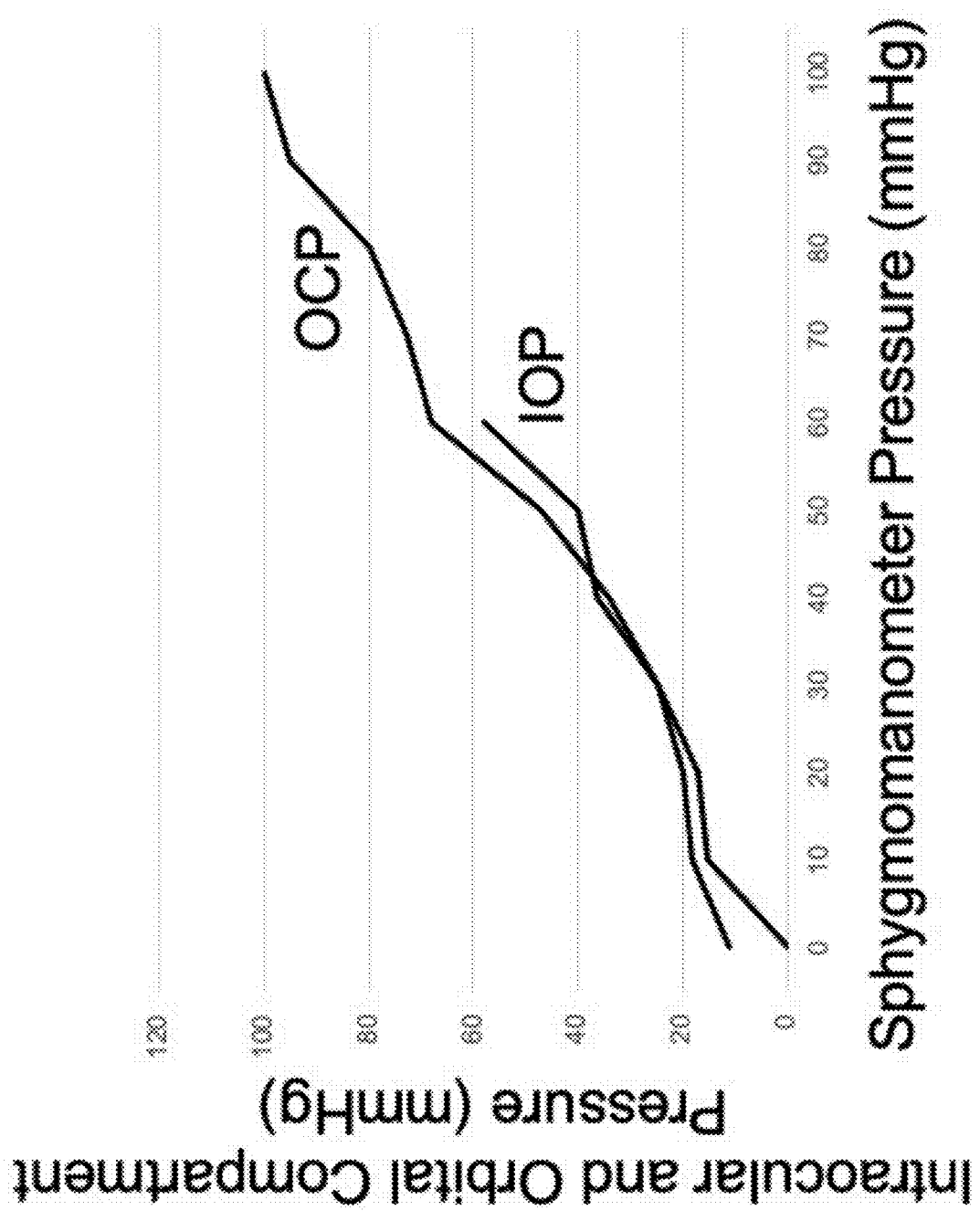
FIG. 6 shows according to an exemplary embodiment of the invention a graph correlating sphygmomanometer pressure with intraocular pressure (IOP, measured by a digital tonometer) and OCP (measured by the pressure sensing retractor). Is it noted that the digital tonometer was unable to measure sphygmomanometer pressures greater than 60 mmHg.

FIG. 1 shows an example of an embodiment of the pressure sensing retractor for measuring orbital compartment pressure of an eye. Two retractor blades can be distinguished. First, an inner retractor blade that has a section with a proximal end and a distal end. At the distal end, the inner retractor blade has an inner claw-like curved retractor with an inner-claw radius. Second, an outer retractor blade that has a section with a proximal end and a distal end. At the distal end, the outer retractor blade has an outer claw-like curved retractor with an outer-claw radius. The outer-claw radius is larger than the inner-claw radius such that the inner claw-like curved retractor is nested with the outer claw-like curved retractor while maintaining a separation distance as shown in FIGS. 1-3. In one example, the sections of the inner retractor blade and the outer blade are linear sections.

Further, the pressure sensing retractor has a force sensor with a first end and a second end. The proximal end of the outer retractor blade is connected to the first end of the force sensor, and the distal end of the inner retractor blade is connected to the second end of the force sensor. In the example of FIG. 1 the force sensor is a parallel beam load cell, but other types of force sensors can be used as well like a force compression sensor, a torque sensor, or the like. Variations in the type of force sensor might change the structural design of the pressure sensing retractor, however, the principle of the nested claws remains the same as that is key to the operation of the pressure sensing retractor as a continuous measurement device.

In the example of the parallel beam load cell containing strain gauges in a Wheatstone bridge configuration, the parallel beam load cell can be anchored to a handle, which also serves as a shim to separate the inner and outer retractor blades (FIG. 1).

The force sensor or load cell can be spliced to interface wires, wrapped with electrical heat shrink tubing and connected to an amplifier/microcontroller. The force sensor or load cell output can be calibrated to correspond with mmHg values permitting the use of familiar metrics for clinical decision making.

The inner claw-like curved retractor is capable of pulling an eyelid of the eye, while the outer claw-like curved retractor is capable of sensing the orbital compartment pressure of the eye. The separation distance between the claw-like ends is sufficient to permit a compression or a force sensor change without the inner retractor blade and the outer retractor blade contact at forces exceeding an equivalent of 100 mmHg of an orbital compartment pressure.

In one example of this embodiment, the retractor blades are 12 mm wide and the blades are separated by 1.5 mm, though this latter measure could be even lower if one uses blade materials with less deflection. It was found that a 500-gram load cell was far in excess of the capacity that one would need to measure orbital compartment pressures exceeding 100 mmHg. Typical clinical compartment syndromes rarely exceed 80-90 mmHg.

A disposable (latex) sleeve could be fitted over each of the nested claw tips, permitting clean use for each patient. Similarly, disposable sleeves could be fitted over the inner retractor blade and the outer retractor blade in addition to the claws.

The present invention further provides a method of measuring orbital compartment pressure in an eye using the pressure sensing retractor embodiments described infra. When a patient is presented, the pressure sensing retractor is placed in between an eyelid and a globe of the eye. Using the handle, the eyelid of the eye is pulled by the inner claw-like curved retractor. The force sensor then is capable of sensing the orbital compartment pressure via the globe of the eye with or via the outer claw-like curved retractor where the globe of the eye presses on the outer claw-like curved retractor. Collected sensory data is processed if needed and outputted as a continuous signal of the orbital compartment pressure of the eye.

In an example of use, the pressure sensing retractor may be placed beneath the lower eyelid when canthotomy/cantholysis is being performed, and the sensed pressure drops dramatically in real time when the tarsoligamentous sling is appropriately released, obviating the need for serial TOP measurements. The pressure sensing retractor can then be placed under the upper eyelid to evaluate the residual orbital compartment pressure and to determine whether superior cantholysis or other additional interventions are required.

What is claimed is:

1. A pressure sensing retractor for measuring orbital compartment pressure of an eye, comprising:

(a) an inner retractor blade comprising (i) a section with a proximal end and a distal end, and (ii) at the distal end of the inner retractor blade an inner curved retractor blade with an inner radius;

(b) an outer retractor blade comprising (j) a section with a proximal end and a distal end, and (jj) at the distal end of the outer retractor blade an outer curved retractor blade with an outer radius, wherein the outer radius is larger than the inner radius such that the inner curved retractor blade is nested within the outer curved retractor blade while maintaining a separation distance; and (c) a force sensor with a first end and a second end, wherein the proximal end of the outer retractor blade is connected to the second end of the force sensor, and wherein the proximal end of the inner retractor blade is connected to the first end of the force sensor.

2. The pressure sensing retractor as set forth in claim 1, wherein the separation distance is sufficient to permit a compression or a force sensor change without the inner retractor blade and the outer retractor blade contact at forces exceeding an equivalent of 100 mmHg of an orbital compartment pressure.

3. The pressure sensing retractor as set forth in claim 1, wherein the sections of the inner retractor blade and the outer blade are linear sections and positioned substantially parallel with respect to each other.

4. The pressure sensing retractor as set forth in claim 1, further comprising disposable sleeves for the inner retractor blade and the outer retractor blade.

5. The pressure sensing retractor as set forth in claim 1, further comprising disposable sleeves for the inner curved retractor blade and the outer curved retractor blade.

6. The pressure sensing retractor as set forth in claim 1, further comprising a handle to which the first end of the force sensor and the proximal end of the inner retractor blade are connected.

7. The pressure sensing retractor as set forth in claim 1, wherein the inner curved retractor blade is capable of pulling an eyelid of the eye, while the outer curved retractor blade is capable of touching the orbital compartment pressure of the eye, wherein the touching is registered by the force sensor.

8. The pressure sensing retractor as set forth in claim 1, wherein the force sensor is a parallel beam load cell, a force compression sensor, or a torque sensor.

9. A method of measuring orbital compartment pressure in an eye, comprising:
(a) having a pressure sensing retractor comprising:
an inner retractor blade comprising (i) a section with a proximal end and a distal end, and (ii) at the distal end of the inner retractor blade an inner curved retractor blade with an inner radius,
an outer retractor blade comprising (j) a linear section with a proximal end and a distal end, and (jj) at the distal end of the outer retractor blade an outer curved retractor blade with an outer radius, wherein the outer radius is larger than the inner radius such that the inner curved retractor blade is nested within the outer curved retractor while maintaining a separation distance, and
a force sensor with a first end and a second end, wherein the proximal end of the outer retractor blade is connected to the second end of the force sensor, and wherein the proximal end of the inner retractor blade is connected to the first end of the force sensor;
(b) placing the pressure sensing retractor in between an eyelid and a globe of the eye;
(c) pulling with the inner curved retractor blade the eyelid of the eye; and
(d) touching with the outer curved retractor blade the orbital compartment pressure via the globe of the eye, wherein the touching is registered by the force sensor.

10. The method as set forth in claim 9, further comprising outputting a continuous signal of the orbital compartment pressure of the eye.

11. The method as set forth in claim 9, further comprising adding disposable sleeves to the inner retractor blade and the outer retractor blade.

12. The method as set forth in claim 9, further comprising disposable sleeves to the inner curved retractor blade and the outer curved retractor blade.

* * * * *